(12) United States Patent
Heywood et al.

(10) Patent No.: US 10,832,816 B2
(45) Date of Patent: Nov. 10, 2020

(54) PERSONALIZED MANAGEMENT AND MONITORING OF MEDICAL CONDITIONS

(71) Applicant: PatientsLikeMe, Inc., Cambridge, MA (US)

(72) Inventors: Benjamin Heywood, Cambridge, MA (US); James Heywood, Newton, MA (US); Paul Wicks, Wokingham (GB)

(73) Assignee: PatientsLikeMe, Inc., Cambridge, MA (US)

( * ) Notice: Subject to any disclaimer, the term of this patent is extended or adjusted under 35 U.S.C. 154(b) by 661 days.

(21) Appl. No.: 14/952,432

(22) Filed: Nov. 25, 2015

(65) Prior Publication Data

US 2016/0188807 A1    Jun. 30, 2016

Related U.S. Application Data

(63) Continuation of application No. 12/250,889, filed on Oct. 14, 2008, now abandoned.

(51) Int. Cl.
*G16H 50/20*    (2018.01)
*G06F 19/00*    (2018.01)
(Continued)

(52) U.S. Cl.
CPC .......... *G16H 50/20* (2018.01); *A61B 5/0002* (2013.01); *A61B 5/4824* (2013.01);
(Continued)

(58) Field of Classification Search
CPC ......... G06Q 50/22; G16H 10/60; G16H 50/20
See application file for complete search history.

(56) References Cited

U.S. PATENT DOCUMENTS 3,934,226 A    1/1976  Stone et al.
4,712,562 A    12/1987 Ohayon et al.
(Continued)

FOREIGN PATENT DOCUMENTS

DE    3703404 C    3/1923
EP    0912957 B1   12/2004
(Continued)

OTHER PUBLICATIONS

U.S. Appl. No. 12/250,889, filed Oct. 14, 2008, 2009/0144089A1, Jun. 4, 2009, Personalized Management and Monitoring of Medical Conditions.

(Continued)

*Primary Examiner* — Robert A Sorey
*Assistant Examiner* — Kristine K Rapillo
(74) *Attorney, Agent, or Firm* — Greenberg Traurig, LLP; David J. Dykeman

(57) ABSTRACT

The invention provides a system and a method for tracking, assessing, and managing personalized data related to medical conditions, diseases, disease symptoms, treatments, body function metrics, health and well-being, education, and training. In one embodiment, a method for personalized management of a medical condition is provided. The method includes providing a graphical user interface for allowing the patient to input at least one medical condition metric and at least one intervention, receiving at least one medical condition metric for a patient for a time interval, receiving information about at least one intervention for the patient for the time interval, and displaying the at least one medical condition metric and intervention over the time interval.

10 Claims, 9 Drawing Sheets

(51) Int. Cl.

| | | |
|---|---|---|
| *G16H 40/63* | (2018.01) | |
| *G16H 50/70* | (2018.01) | |
| *G16H 50/50* | (2018.01) | |
| *G16H 15/00* | (2018.01) | |
| *G16H 10/60* | (2018.01) | |
| *A61B 5/00* | (2006.01) | |
| *G06Q 50/22* | (2018.01) | |
| *G06Q 50/24* | (2012.01) | |
| *G16H 10/20* | (2018.01) | |
| *G16H 40/20* | (2018.01) | |
| *G16H 20/40* | (2018.01) | |
| *G16H 20/10* | (2018.01) | |

(52) U.S. Cl.
CPC .......... *A61B 5/4833* (2013.01); *G06F 19/325* (2013.01); *G06Q 50/22* (2013.01); *G06Q 50/24* (2013.01); *G16H 10/20* (2018.01); *G16H 10/60* (2018.01); *G16H 15/00* (2018.01); *G16H 40/20* (2018.01); *G16H 40/63* (2018.01); *G16H 50/50* (2018.01); *G16H 50/70* (2018.01); *G06F 19/3456* (2013.01); *G06F 19/3481* (2013.01); *G16H 20/10* (2018.01); *G16H 20/40* (2018.01)

(56) References Cited

U.S. PATENT DOCUMENTS

| | | |
|---|---|---|
| 4,899,839 A | 2/1990 | Dessertine et al. |
| 5,014,798 A | 5/1991 | Glynn |
| 5,025,374 A | 6/1991 | Roizen et al. |
| 5,549,117 A | 8/1996 | Tacklind et al. |
| 5,594,637 A | 1/1997 | Eisenberg et al. |
| 5,626,144 A | 5/1997 | Tacklind et al. |
| 5,653,739 A | 8/1997 | Maurer et al. |
| 5,692,215 A | 11/1997 | Kutzik et al. |
| 5,692,500 A | 12/1997 | Gaston-Johansson |
| 5,704,366 A | 1/1998 | Tacklind et al. |
| 5,713,350 A | 2/1998 | Yokota et al. |
| 5,720,502 A | 2/1998 | Cain |
| 5,732,709 A | 3/1998 | Tacklind et al. |
| 5,778,882 A | 7/1998 | Raymond et al. |
| 5,812,983 A | 9/1998 | Kumagai |
| 5,830,149 A * | 11/1998 | Oka .................. A61B 5/02116 600/500 |
| 5,838,313 A | 11/1998 | Hou et al. |
| 5,937,387 A | 8/1999 | Summerell et al. |
| 5,950,168 A | 9/1999 | Simborg et al. |
| 5,984,368 A | 11/1999 | Cain |
| 5,991,729 A | 11/1999 | Barry et al. |
| 6,024,699 A | 2/2000 | Surwit et al. |
| 6,032,119 A | 2/2000 | Brown et al. |
| 6,067,523 A | 5/2000 | Bair et al. |
| 6,081,786 A | 6/2000 | Barry et al. |
| 6,102,874 A | 8/2000 | Stone et al. |
| 6,108,635 A | 8/2000 | Herren et al. |
| 6,108,685 A | 8/2000 | Kutzik et al. |
| 6,113,552 A | 9/2000 | Shimazu et al. |
| 6,168,569 B1 | 1/2001 | McEwen et al. |
| 6,186,145 B1 | 2/2001 | Brown |
| 6,231,560 B1 | 5/2001 | Bui et al. |
| 6,234,964 B1 | 5/2001 | Iliff |
| 6,235,964 B1 | 5/2001 | Kadash et al. |
| 6,236,983 B1 | 5/2001 | Hofmann et al. |
| 6,246,992 B1 | 6/2001 | Brown |
| 6,277,072 B1 | 8/2001 | Bardy |
| 6,282,441 B1 | 8/2001 | Raymond et al. |
| 6,283,923 B1 | 9/2001 | Finkelstein et al. |
| 6,294,999 B1 | 9/2001 | Yarin et al. |
| 6,314,405 B1 | 11/2001 | Richardson |
| 6,322,504 B1 | 11/2001 | Kirshner |
| 6,332,504 B1 | 12/2001 | Adds |
| 6,334,192 B1 | 12/2001 | Karpf |
| 6,335,907 B1 | 1/2002 | Momich et al. |
| 6,339,410 B1 | 1/2002 | Milner et al. |
| 6,380,858 B1 | 4/2002 | Yarin et al. |
| 6,400,996 B1 | 6/2002 | Hoffberg et al. |
| 6,405,034 B1 | 6/2002 | Tijerino |
| 6,484,144 B2 | 11/2002 | Martin et al. |
| 6,529,195 B1 | 3/2003 | Eberlein |
| 6,560,541 B1 | 5/2003 | Singh |
| 6,587,829 B1 | 7/2003 | Camarda et al. |
| 6,589,169 B1 | 7/2003 | Surwit et al. |
| 6,611,846 B1 | 8/2003 | Stoodley |
| 6,612,985 B2 | 9/2003 | Eiffert et al. |
| 6,690,397 B1 | 2/2004 | Daignault, Jr. |
| 6,723,045 B2 | 4/2004 | Cosentino et al. |
| 6,770,029 B2 | 8/2004 | Iliff |
| 6,789,091 B2 | 9/2004 | Gogolak |
| 6,802,810 B2 | 10/2004 | Ciarniello et al. |
| 6,856,315 B2 | 2/2005 | Eberlein |
| 6,915,170 B2 | 7/2005 | Engleson et al. |
| 6,929,607 B2 | 8/2005 | Lipman |
| 6,956,572 B2 | 10/2005 | Zaleski |
| 6,970,742 B2 | 11/2005 | Mann et al. |
| 6,980,958 B1 | 12/2005 | Surwit et al. |
| 6,988,075 B1 | 1/2006 | Hacker |
| 6,999,890 B2 | 2/2006 | Kai |
| 7,029,441 B2 | 4/2006 | Dodds |
| 7,039,878 B2 | 5/2006 | Auer et al. |
| 7,054,758 B2 | 5/2006 | Gill-Garrison et al. |
| 7,066,883 B2 | 6/2006 | Schmidt et al. |
| 7,107,547 B2 | 9/2006 | Cule et al. |
| 7,137,951 B2 | 11/2006 | Pilarski |
| 7,165,221 B2 | 1/2007 | Monteleone et al. |
| 7,169,085 B1 | 1/2007 | Killin et al. |
| 7,251,609 B1 | 7/2007 | McAlindon et al. |
| 7,286,997 B2 | 10/2007 | Spector et al. |
| 7,287,031 B1 | 10/2007 | Karpf et al. |
| 7,302,398 B2 | 11/2007 | Ban et al. |
| 7,330,818 B1 | 2/2008 | Ladocsi et al. |
| 7,428,494 B2 | 9/2008 | Hasan et al. |
| 7,761,311 B2 * | 7/2010 | Clements ............ G06F 19/3456 705/3 |
| 8,160,901 B2 | 4/2012 | Heywood et al. |
| 8,643,648 B2 | 2/2014 | Heywood et al. |
| 8,930,224 B2 | 1/2015 | Heywood et al. |
| 9,270,632 B2 | 2/2016 | Heywood et al. |
| 9,589,104 B2 | 3/2017 | Heywood et al. |
| 9,589,251 B2 | 3/2017 | Heywood et al. |
| 10,402,916 B2 | 9/2019 | Heywood et al. |
| 10,665,344 B2 | 5/2020 | Heywood et al. |
| 2001/0034639 A1 | 10/2001 | Jacoby et al. |
| 2002/0072933 A1 | 6/2002 | Vonk et al. |
| 2002/0150872 A1* | 10/2002 | Glenn ................ G16H 10/60 434/236 |
| 2003/0023461 A1* | 1/2003 | Quintanilla ........... G06F 19/324 705/3 |
| 2003/0125609 A1 | 7/2003 | Becker |
| 2003/0163353 A1 | 8/2003 | Luce et al. |
| 2003/0187683 A1 | 10/2003 | Kirchhoff et al. |
| 2004/0015337 A1 | 1/2004 | Thomas et al. |
| 2004/0030741 A1 | 2/2004 | Wolton et al. |
| 2004/0064447 A1 | 4/2004 | Simske et al. |
| 2004/0078237 A1* | 4/2004 | Kaafarani ............ G06Q 50/22 705/2 |
| 2004/0122707 A1 | 6/2004 | Sabol et al. |
| 2004/0161143 A1* | 8/2004 | Dietz ................ G01N 15/1475 382/133 |
| 2004/0210458 A1 | 10/2004 | Evans et al. |
| 2005/0080462 A1 | 4/2005 | Jenkins et al. |
| 2005/0085866 A1 | 4/2005 | Tehrani |
| 2005/0102160 A1 | 5/2005 | Brown |
| 2005/0108051 A1 | 5/2005 | Weinstein |
| 2005/0144042 A1 | 6/2005 | Joffe et al. |
| 2005/0191716 A1 | 9/2005 | Surwit et al. |
| 2005/0197545 A1 | 9/2005 | Hoggle |
| 2005/0197553 A1 | 9/2005 | Cooper |
| 2005/0272640 A1 | 12/2005 | Doyle et al. |
| 2005/0283384 A1 | 12/2005 | Hunkeler et al. |
| 2005/0283385 A1 | 12/2005 | Hunkeler et al. |
| 2005/0285746 A1 | 12/2005 | Sengupta et al. |
| 2006/0009810 A1 | 1/2006 | Mann et al. |

(56) References Cited

U.S. PATENT DOCUMENTS

| | | | |
|---|---|---|---|
| 2006/0010098 A1 | 1/2006 | Goodnow et al. | |
| 2006/0020175 A1 | 1/2006 | Berry et al. | |
| 2006/0030890 A1 | 2/2006 | Cosentino et al. | |
| 2006/0031101 A1 | 2/2006 | Ross | |
| 2006/0036134 A1 | 2/2006 | Tarassenko et al. | |
| 2006/0036294 A1 | 2/2006 | Tehrani | |
| 2006/0036619 A1 | 2/2006 | Fuerst et al. | |
| 2006/0052945 A1 | 3/2006 | Rabinowitz et al. | |
| 2006/0064030 A1 | 3/2006 | Cosentino et al. | |
| 2006/0085217 A1 | 4/2006 | Grace | |
| 2006/0089540 A1 | 4/2006 | Meissner | |
| 2006/0122468 A1 | 6/2006 | Tavor | |
| 2006/0249423 A1 | 11/2006 | Reijonen | |
| 2007/0005393 A1 | 1/2007 | Cole et al. | |
| 2007/0015974 A1 | 1/2007 | Higgins et al. | |
| 2007/0021979 A1 | 1/2007 | Cosentino et al. | |
| 2007/0021984 A1 | 1/2007 | Brown | |
| 2007/0048691 A1 | 3/2007 | Brown | |
| 2007/0060803 A1 | 3/2007 | Liljeryd et al. | |
| 2007/0061166 A1 | 3/2007 | Ramasubramanian et al. | |
| 2007/0115282 A1 | 5/2007 | Turner et al. | |
| 2007/0239416 A1* | 10/2007 | Saito | G16C 20/30 703/11 |
| 2007/0250134 A1* | 10/2007 | Miesel | A61B 5/1038 607/45 |
| 2008/0010089 A1 | 1/2008 | Dimaggio et al. | |
| 2008/0091084 A1 | 4/2008 | Yudkovitch et al. | |
| 2008/0119958 A1 | 5/2008 | Bear et al. | |
| 2008/0200771 A1 | 8/2008 | Brown | |
| 2008/0201174 A1 | 8/2008 | Ramasubramanian et al. | |
| 2008/0249806 A1* | 10/2008 | Dlugos | A61F 5/0003 705/3 |
| 2009/0144089 A1 | 6/2009 | Heywood et al. | |
| 2016/0188807 A1 | 6/2016 | Heywood et al. | |
| 2017/0206327 A1 | 7/2017 | Heywood et al. | |
| 2019/0347744 A1 | 11/2019 | Heywood et al. | |

FOREIGN PATENT DOCUMENTS

| | | |
|---|---|---|
| WO | 200029983 A1 | 5/2000 |
| WO | 200150950 A2 | 7/2001 |

OTHER PUBLICATIONS

Baum et al., "A Maximization Technique Occurring in the Statistical Analysis of Probabilistic Functions of Markov Chains," Annals of Mathematical Statistics, 1970, vol. 41, No. 1, pp. 164-171.

Cedarbaum et al., "Performance of the Amyotrophic Lateral Sclerosis Functional Rating Scale (ALSFRS) in multicenter clinical trials," Journal of the Neurological Sciences, Oct. 1997, vol. 152, Supplement 1, pp. S1-S9.

Cedarbaum et al., "The ALSFRS-R: a revised ALS functional rating scale that incorporates assessments of respiratory function," Journal of the Neurological Sciences, 1999, vol. 169, pp. 13-21.

Cudkowicz et al., "Measures & Markers in Amyotrophic Lateral Sclerosis," NeuroRx, Apr. 2004, vol. 1, pp. 273-283.

Dayhoff et al., "Providing a Complete Online Multimedia Patient Record," AMIA, Inc., 1999, pp. 241-245.

Deneault et al., "An Integrative Display for Patient Monitoring," IEEE International Conference on Systems, Man & Cybernetics Conference Proceedings, 1990, pp. 515-517.

Emmons et al., "Counting Blessings Versus Burdens: An Experimental Investigation of Gratitude and Subjective Well-Being in Daily Life," Journal of Personality and Social Psychology, 2003, vol. 84, No. 2, pp. 377-389.

Fornai et al., "Lithium delays progression of amyotrophic lateral sclerosis," Proceedings of the National Academy of Sciences, Feb. 12, 2008, vol. 105, No. 6, pp. 2052-2057.

Frost et al., "Social Uses of Personal Health Information Within PatientsLikeMe, an Online Patient Community: What Can Happen When Patients Have Access to One Another's Data," Journal of Medical Internet Research, May 27, 2008, vol. 10, No. 3, p. e15.

Goetz, "Practicing Patients," The New York Times Magazine, Mar. 23, 2008.

Gordon, "Advances in Clinical Trials for Amyotrophic Lateral Sclerosis," Current Neurology & Neuroscience Reports, 2005, vol. 5, pp. 48-54.

Gordon et al., "Progression rate of ALSFRS-R at time of diagnosis predicts survival time in ALS," Neurology, Oct. 2006, vol. 67, pp. 1314-1315.

Kasarskis et al., "Rating the severity of ALS by caregivers over the phone using ALSFRS-R," Amyotrophic Lateral Sclerosis & Other Motor Neuron Disorders, 2004, vol. 5, Supplement 2, p. 12.

Kasarskis et al., "Rating the severity of ALS by caregivers over the phone using ALSFRS-R," Amyotrophic Lateral Sclerosis, Mar. 2005, vol. 6, Iss. 1, pp. 50-54.

Litt et al., "Graphical Representation of Medical Information in the Visual Chart," Seventh Annual IEEE Symposium on Computer-Based Medical Systems, 1994, pp. 252-257.

Long et al., "Web Interface for the Heart Disease Program," Proceedings: AMIA Symposium, 1996, pp. 762-766.

Marquardt, "An Algorithm for Least-Squares Estimation of Non-linear Parameters," Journal of the Society for Industrial and Applied Mathematics, Jun. 1963, vol. 11, Iss. 2, pp. 431-441.

Miller et al., "Is the ALSFRS-R Rate of Decline Linear Over Time?," Amyotrophic Lateral Sclerosis, Jan. 2007, vol. 8, Supplement 1, pp. 140-155.

Montes et al., "Development & Evaluation of self-administered version of the ALSFRS-R," Neurology, Oct. 2006, vol. 67, pp. 1294-1296.

Ogura et al., "Clinical Trial of Risedronate in Japanese Volunteers: A Study on the Effects of Timing of Dosing on Absorption," Journal of Bone and Mineral Metabolism, 2004, vol. 22, pp. 120-126.

Orimo et al., "Graphical Output of Health Testing Data," Medical Informatics, 1990, vol. 15, Iss. 2, pp. 141-149.

"Pediatric Research Program Issue APS-SPR," San Diego Convention Center, San Diego, CA, May 7-11, 1995, vol. 37, No. 4 Part 2, p. 139A (Apr. 1995).

Seligman et al., "Positive Psychology Progress," American Psychologist, Jul.-Aug. 2005, pp. 410-421.

U.S. FDA, "Guideline for Industry: Dose Response Information to Support Drug Registration," U.S. FDA; Federal Register, Nov. 9, 1994, vol. 59, No. 216.

International Search Report for International Patent Application No. PCT/US08/79672, dated Dec. 16, 2008.

Non-Final Office Action for corresponding U.S. Appl. No. 12/251,031, dated Aug. 9, 2010.

Non-Final Office Action for corresponding U.S. Appl. No. 12/251,031, dated Feb. 16, 2011.

Written Opinion of the International Searching Authority for International Patent Application No. PCT/US08/79672, dated Dec. 16, 2008.

* cited by examiner

PERSONALIZED MANAGEMENT AND MONITORING OF MEDICAL CONDITIONS

RELATED APPLICATION

This application is a Continuation of U.S. patent application Ser. No. 12/250,889 filed on Oct. 14, 2008.

TECHNICAL FIELD

The invention relates to the tracking and assessment of personalized data related to medical conditions, body function, health and well-being.

BACKGROUND OF THE INVENTION

The advent of the World Wide Web offers new opportunities for people to share information, opinions, and experiences on virtually any topic. With the support of web-based systems and methodologies, people with common goals and interests can interact and communicate instantaneously from anywhere on the globe. For example, people can use a computer dating web site to search for a compatible mate. A person can create an account on the web site and enter personal information which is stored in a user profile in a database. The database contains profiles of other persons who use the web site. A person can search for a compatible mate by entering information on characteristics they seek in their mate. The web site can process the search criteria and return a list of matching profiles. The person can then obtain further information and contact a potential mate.

Many web sites exist to serve a particular group of people who share common goals or attributes. For example, U.S. Patent Publication No. 2003/0187683 describes a system for establishing weight control programs. The system allows persons to enter, update, and monitor their weight, and permits users to share recipes and establish meal plans. U.S. Pat. No. 7,029,441 describes a system for comparing non-human animal subjects by animal breed or genetic disposition. For example, laboratory test results for a non-human animal subject can be compared with genetic data for the group.

The existing art includes examples of systems for monitoring patient information to assist in providing medial care. U.S. Pat. No. 6,956,572 describes a system for monitoring patients for critical care. The system includes sliders for setting maximum and minimum thresholds for a particular medical parameter for a patient and the current value for the parameter. This allows the medical staff to quickly determine whether or not a patient's condition is normal. Another example, the LifeLines software from the University of Maryland Human-Computer Interaction Lab of College Park, Md., is a system for visualizing medical history records, which allows medical personnel to examine medical history records in detail. The system includes visual tools such as timelines and icons to denote past events in the medical history.

SUMMARY OF THE INVENTION

The invention provides a method for personalized management of a medical condition. The method includes providing a graphical user interface for allowing the patient to input at least one medical condition metric and at least one intervention, receiving at least one medical condition metric for a patient for a time interval, receiving information about at least one intervention for the patient for the time interval, and displaying the at least one medical condition metric and intervention over the time interval.

The at least one medical condition metric can be observed by the patient. The method can also include receiving an additional medical condition metric measured by a medical device. The intervention can include administration of a medication, administration of a remedy, administration of a nutritional supplement, administration of a vitamin, exercise, physical therapy, massage, stretching, consumption of food, rest, and sleep.

The chart can include pharmacokinetic data for the medication. The graphical element can be a chart. The chart can be a line chart. Time can be depicted on the x-axis of the chart. The time interval can be one selected from the group consisting of: 24 hours, 1 week, and 1 month. The chart can display data from multiple time periods.

The graphical element can include displaying a plurality of charts. Each of the plurality of charts can display information for a different time interval. The graphical element can include a slider bar for inputting a medical condition metric.

The method of can also include the step of calculating a correlation between the at least one intervention and the at least one medical condition metric.

The medical condition can be selected from the group consisting of: movement disorders including parkinsonism, pain disorders including back pain, migraines, fibromyalgia, fatigue disorders, mood disorders including depression and anxiety, eating disorders, and seizure disorders including epilepsy.

The at least one medical condition metric can be received from a mobile device.

The time interval can be an actual time interval or a representative time interval. The medical condition metric can be an actual medical condition metric or a representative medical condition metric.

The invention also provides a method of determining the interaction between an intervention and a medical condition metric in a patient. The method includes the steps of: obtaining a record of at least one medical condition metric over a predetermined time interval, obtaining a record of interventions over the same predetermined time interval, illustrating the record of said medical condition metric and the record of said intervention over a selected time interval that encompasses at least part of said predetermined time interval in a graphic display, and permitting said patient to manipulate said graphic display and the data contained therein to modify the data and determine correlations between such data. The method enables a determination of the interaction between said intervention and said medical condition metric.

The invention also provides a computer-readable medium whose contents cause a computer to perform a method for personalized management of a medical condition. The method includes: providing a graphical user interface for allowing the patient to input at least one medical condition metric and at least one intervention, receiving at least one medical condition metric for a patient for a time interval, receiving information about at least one intervention for the patient for the time interval, and displaying the at least one medical condition metric and intervention over the time interval.

The invention also provides a computer-readable medium whose contents cause a computer to perform a method of determining the interaction between an intervention and a medical condition metric in a patient. The method includes the steps of: obtaining a record of at least one medical condition metric over a predetermined time interval; obtaining a record of interventions over the same predetermined time interval; illustrating the record of said medical condition metric and the record of said intervention over a selected time interval that encompasses at least part of said predetermined time interval in a graphic display; and permitting said patient to manipulate said graphic display and the data contained therein to modify the data and determine correlations between such data. Through the use of the computer-readable medium, the interaction between said intervention and said medical condition metric can be determined.

The invention also provides a method of treating a depressed patient. The method includes providing a graphical user interface for allowing the patient to input at least one medical condition metric, receiving at least one medical condition metric for a patient for a time interval, displaying the at least one medical condition metric and intervention over the time interval. The time interval can include at least one period in which the patient was not experiencing a depressive episode.

The medical condition metric can be the patient's mood. The medical condition metric can be a rating scale. The method can also include collecting at least one medical condition before the patient is diagnosed with depression.

The invention is also directed to a system and a method for tracking and assessing personalized data related to a medical condition. The medical condition can be related to a disease, disease symptom, body function, health and well-being. The invention can permit a person, for example, a patient diagnosed with Amyotrophic Lateral Sclerosis (ALS), to enter data related to his ALS, for example, how well he is feeling over the course of a particular day, treatments he is taking, and other daily activities, such as meals. For example, the patient can wake up in the morning feeling nauseous. After a morning meal, the person make take a first dose of his medication. By the later morning, his nausea may pass and he may feel better. He can exercise in late morning and have lunch. By mid-afternoon, his nausea may return and he can take a short nap. After waking from his nap, he may feel better and take a second dose of his medication. He can have a light dinner and do some house chores. Later in the evening, he may feel exhausted and go to bed. After few hours of sleep, he make awake feeling very nauseous. The patient can use the invention to track and record his feeling of well-being at various times throughout his day and for a number of different days. He can also track and record his treatments, meals, and other daily activities, such as exercise. In this way, he can better self-assess and manage his ALS. For example, he may note that taking the first dose of his treatment in the morning when he wakes up, followed by a light meal tends to reduce his nausea, whereas if he waits until mid-morning, the nausea continues for another few hours.

The invention can include the steps of providing a user interface for entering medical condition metrics for a medical condition, storing the metrics, analyzing the metrics, and providing a graphical element to display and visualize the metrics. The graphical element can include a time scale, a metric scale, a range of values for the metric, and a plurality of points. Each point can represent an entered medical condition metric for the medical condition. The point can be displayed in the graphical element at a position corresponding to the metric value and the time the metric was taken.

The method can further include providing a patient profile. A patient profile can include one of the medical condition metrics. A patient profile can further include other personalized data about a patient, including name, sex, and age. The method can further include providing a medical outcome correlation. In this embodiment, the step of storing can include storing the patient profile and displaying the medical outcome correlation in the graphical element.

The step of providing the user interface can further include providing a point movement means for moving metric points displayed in the graphical element. The points can be moved within the range of metric values. The point movement means can be a graphical slider. The point movement means can further include an input from a user.

The method can further include the step of providing a line for joining the adjacent points for each metric. The line can be a polyline of separate line segments, each segment joining adjacent metric points. The step of providing a line can further include providing multiple lines, each line joining adjacent points related to a medical condition metric or a medical outcome correlation.

The graphical element can further include a status element for relating information about one of the metrics. The status element can include a color element and a text message related to the metric.

The graphical element can further include a treatment graphical element for relating information about a treatment for the medical condition. The treatment graphical element can include treatment dosage, treatment name, or treatment frequency. The method using the graphical element can further include the steps of providing a list of treatment graphical elements, selecting one or more treatment graphical elements from the list, dragging the selection, and dropping the selection at a location representing the time the one or more treatments was administered.

The method can further include the steps of providing a minimum medical condition metric value and a maximum medical condition metric value, and providing a center line drawn halfway between the minimum and maximum values.

The time scale can further include a start and an end time. The start and the end time can be about 24 hours apart, about one week apart, about one month apart, or the start and end time can be a time span apart appropriate for the medical condition metric.

The graphical element can further include a daily activity related to the medical condition. The daily activity can relate to eating or exercising.

The invention can include a method including the steps of entering medical condition metrics related to a medical condition, and viewing the medical condition metrics using a graphical element. The graphical element can include a time scale, a metric scale, a range of values for the metric, and a plurality of points. Each point can represent an entered medical condition metric for the medical condition. The point can be displayed in the graphical element at a position corresponding to the metric value and the time the metric was taken.

The method can further include the steps of entering a medical outcome correlation for the medical condition and viewing the medical outcome correlation using the graphical element.

The invention can provide a computer-readable memory device encoded with a data structure for transferring data between a client program and a server program during a procedure call. The server program can include functions for invocation by the client program. The functions can include one or more parameters. The data structure can include personalized data. The personalized data can include a patient profile, a medical condition metric, and a medical condition outcome. The personalized data can correspond to one of the parameters transferred from the client program to the server program when one of the functions is invoked.

The invention can include a computer-readable memory device for storing a web-based data processing system including a client software program and a server software program. The client software program can include a user interface for entering a plurality of medical condition metrics related to a medical condition. The client software program can invoke procedure calls of the server computer program. The invocation can occur over a network, including the Internet or an intranet.

The server computer program can include function calls for executing the system. The client software program can send a request to store and analyze data, the request including entered data. The entered data can be encapsulated in a data file or a database stored in a memory. The entered data can be analyzed using a microprocessor. The server program can process the request and store and analyze the data. The server program can generate a graphical element for displaying the medical condition metrics and send the graphical element to the client software program. The graphical element can be sent to the client software program as an image. The client software program can display the image. Alternatively, the server software program can send a series of data values representing the graphical element, which the client software program can use to generate and display the graphical element.

DEFINITIONS

The instant invention is most clearly understood with reference to the following definitions:

As used in the specification and claims, the singular form "a," "an," and "the" include plural references unless the context clearly dictates otherwise.

The term "disease" refers to an abnormal condition of an organism that impairs bodily functions. The term disease includes a variety of physical ailments including, but not limited to, neurological diseases (e.g., Amyotrophic Lateral Sclerosis (ALS), Multiple Sclerosis (MS), Parkinson's Disease), Human Immunodeficiency Virus (HIV), Acquired Immune Deficiency Syndrome (AIDS), cancers (e.g., bladder cancer, blood cancer, breast cancer, colorectal cancer, endometrial cancer, leukemia, lung cancer, lymphoma, ovarian cancer, pancreatic cancer, prostate cancer, and skin cancer), diabetes, digestive disorders (e.g., irritable bower syndrome, gastro esophageal reflux disease, and Crohn's Disease), cardiovascular diseases, osteoporosis, chronic obstructive pulmonary disease (COPD), arthritis, allergies, geriatric diseases, and autoimmune diseases (e.g., lupus). The term disease also include mental ailments including, but not limited to, depression, anxiety disorders, post traumatic stress disorder, mood disorders, psychotic disorders, personality disorders, and eating disorders.

The term "medical condition" refers to a manifestation of a disease such as a symptom. For example, if a patient suffers from Amyotrophic Lateral Sclerosis (ALS), the patient may experience one or more medical conditions such as dysphagia (impaired swallowing).

The term "intervention" refers any event that has a positive, negative, or neutral effect on one or more medical conditions. The term intervention includes a variety of activities including, but not limited to, administration of a medication, administration of a remedy, administration of a nutritional supplement, administration of a vitamin, exercise, physical therapy, massage, stretching, consumption of food, rest, and sleep.

DETAILED DESCRIPTION OF THE INVENTION

The invention provides a system and a method for tracking, assessing, and managing personalized data related to medical conditions, diseases, disease symptoms, treatments, body function metrics, health and well-being, education, and training.

The invention provides for the collection, storage, analysis, and graphical display of one or more medical conditions. Such a system allows for the collection of large amounts of data that previously was unavailable to patients, medical professionals, or researchers.

Figure 1:
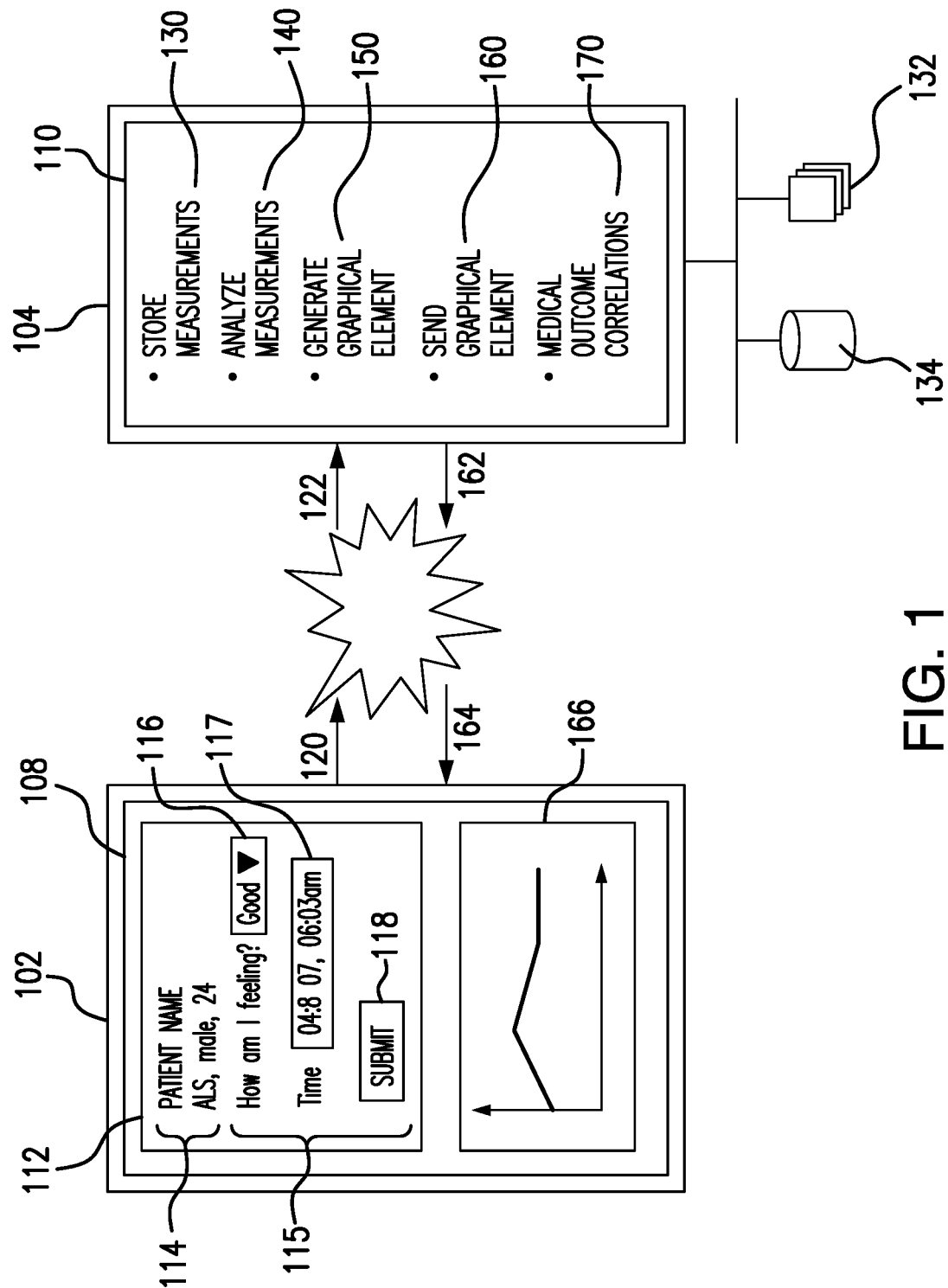
FIG. 1 is a diagram depicting a Internet-based system for personalized management and monitoring of medical conditions.

A web-based data-processing system 100 shown in FIG. 1 can be used to implement a method for practicing the invention. Web-based data-processing systems are well known in the art and can include a client computer 102 and a server computer 104. The client and server computers can be coupled to each other over the Internet 106. Alternatively, the client and server computers can be coupled to each other over an intranet, for example, behind a firewall of a private corporate network. The private corporate network can be the network for a private hospital.

The client computer can include a client software program 108 for executing software applications. The client software program 108 can be an Internet browser such as Internet browsers such as INTERNET EXPLORER®, available from Microsoft Corporation of Redmond, Wash., FIREFOX®, available from the Mozilla Foundation of Mountain View, Calif., or OPERA®, available from Opera Software AS of Oslo, Norway. The Internet browser can display content encoded in a variety of standards such as Hyper Text Markup Language (HTML), and FLASH®, AIR®, and ACROBAT® platforms available from Adobe Systems of San Jose, Calif. User interfaces can include standard web input elements such as text boxes and toggle buttons for entering text and selecting options. The client computer can include input devices, such as a mouse, keyboard, or touch screen for entering information into the user interface.

The client computer need not be a personal computer per se, but rather encompasses devices such as handheld devices, personal digital assistants, and cellular phones. Mobile devices advantageously allow for more frequent data collection as well as reminders for patients to engage in an interventions such as consumption of medication. Suitable mobile device can be specifically constructed for the methods described herein or can be existing mobile devices such a smart phones available under the BLACK-BERRY® trademark from Research in Motion Limited of Waterloo, Ontario, the PALM® trademark from Palm, Inc. of Sunnyvale, Calif., and the IPHONE™ trademark from Apple, Inc. of Cupertino, Calif.

The server computer can include a server software program 110 including a web server, for example, Apache Server, and an application server, for example, Cold Fusion Application Server. The server computer can include a database server or engine for encoding and storing data. Suitable database software includes include DB2® and INFORMIX®, both available from IBM Corp. of Armonk, N.Y.; MICROSOFT JET® and MICROSOFT SQL SERVER® both available from the Microsoft Corp. of Redmond, Wash.; MYSQL® available from the MySQL Ltd. Co. of Stockholm, Sweden; ORACLE® Database, available from Oracle Int'l Corp of Redwood City, Calif.; and SYBASE® available from Sybase, Inc. of Dublin, Calif.

The client software program 108 can be used to provide a user interface 112 for entering personalized data related to a patient, for example, a patient diagnosed with ALS. The personalized data can include patient name, sex, and age 114. The personalized data can include a medical condition metric, for example, whether a patient is feeling great, good, fair, poor, or awful. The personalized data can be submitted to the server software 120 program and the server software program can receive the personalized data 122.

The server program can store the personalized data in memory on the server computer 130. The memory can be used to store a data structure including entries for the personalized data. The data structure can be a structured data file 132 or a relational database 134.

The server software program can analyze the data, for example, using function calls executing on a microprocessor 140. The server software program can generate a graphical element for representing the personalized data 150 and send the graphical element to the client software program 160. The graphical element can be sent (162) over the Internet 106 and received (164) by the client software program. The client software program can display the graphical element 166.

The graphical element can be generated and sent as an image or as a series of values for constructing the graphical element. The image can be sent to the client software program, which can display the image. Alternatively, a series of values can be sent to the client software program, which the client software program can use to construct and display the graphical element. For example, a plug-in executing in an Internet browser can be used to construct and display the graphical element. The plug-in can include special controls for interacting with the graphical element, including sliders for moving medical condition metrics.

The server software program can also store, analyze, generate, and send to the client software program medical outcome correlations 170 for relating aspects of the medical condition, as further explained below.

Figure 2:
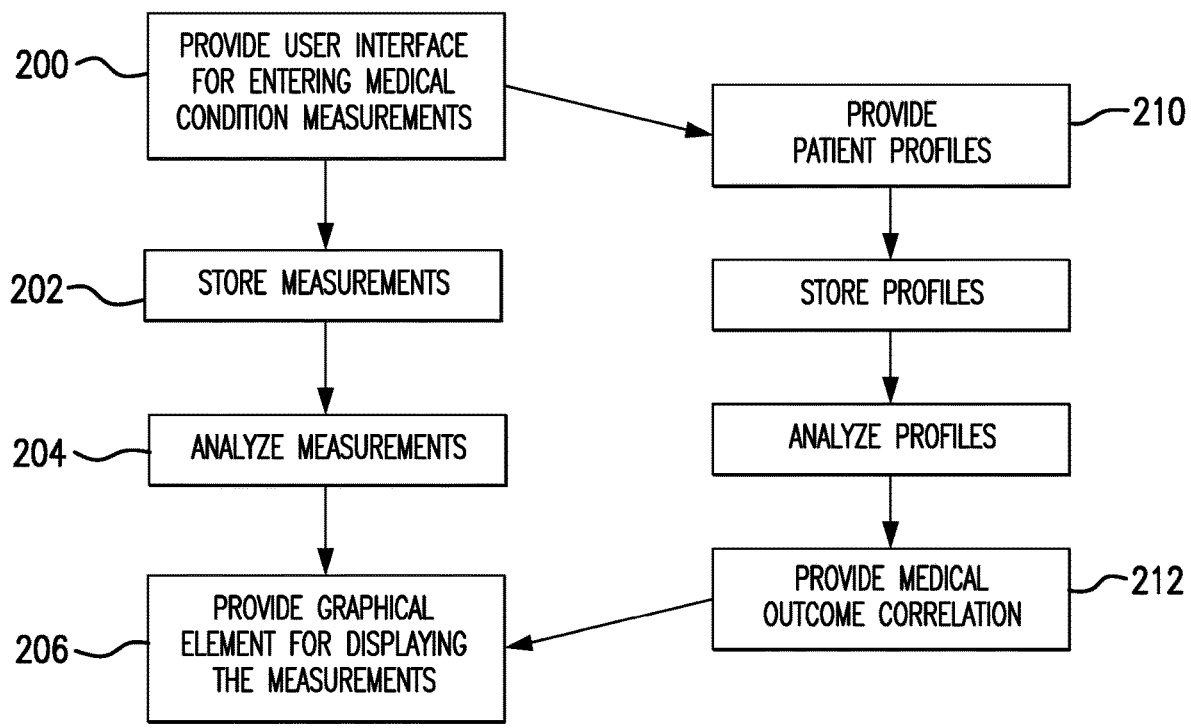
FIG. 2 is a diagram depicting a method of the invention.

As shown in FIG. 2, the method can include the steps of providing a user interface for entering one or more medical condition metrics for a medical condition 200, storing the medical condition metrics 202, analyzing the medical condition metrics 204, and providing a graphical element for displaying the medical system metrics 206.

Medical Condition Metrics

A medical condition metric can be a qualitative or quantitative metric related to a medical condition. For example, a medical condition metric can be a qualitative measure of an ALS patient's feeling of well-being at a particular time of day. The patient may feel great, good, fair, poor, or awful at a particular time of day due to the symptoms and treatments for ALS, and daily activities such as eating and exercising that interact with and affect his condition. Alternatively, the metric can be quantitative in nature, such as blood pressure (e.g., for a patient with heart disease), blood glucose level, pulse, temperature, T-cell count, and the like.

Various rating scales exist to measure medical conditions. In addition to discrete scales such as asking whether the patient feels great/good/fair/poor/awful, numerical scales can be used which ask the patient to quantify one or aspects of their medical condition, for example, on a 1-10 numerical scale. The metric can be a composite metric that produces a numerical representation of the condition based on a series of measurements. Rating scales for measuring depression include the Beck Depression Inventory, the Hamilton Depression Ration Scale, and the Montgomery-Åsberg Depression Rating Scale. Rating scales for assessing ALS patients include the Appel ALS rating scale and the ALS Functional Rating Scale (ALSFRS). Rating scales for Parkinson's Disease include the Unified Parkinson's Disease Rating Scale (UPDRS).

Providing a User Interface

Referring again to FIG. 1, a user interface can be a web page displayed in an Internet browser such as MICROSOFT® INTERNET EXPLORER® (IE) 112. The web page can include standard user interface elements for entering and selecting information 115. The information can include personalized data related to a patient diagnosed with ALS, for example, name, age, sex, type of ALS, symptoms, mobility, etc. 114. The user interface can be used for entering medical condition metrics, such as the patient's assessment of his own feeling of well-being. For example, the user interface can include an option box including the options, "Great", "Good", "Fair", "Poor", and "Awful", and a label next to the box stating "How am I feeling?" 116. Furthermore, the user interface can include an input box for entering a time for the metric, such as "Apr. 25, 2007, 2:25 pm" 117. The user interface can include a button 118 for submitting the entered medical condition metric and time to a server for storage, analysis, and display.

The user interface can also be a text-based interface. For example, the server can send a text message or an email to a cellular phone or a smart phone asking how the patient is feeling. The patient can respond with an appropriate answer.

Likewise, the user interface can be an audio interface in which the server periodically places a telephone call to the patient asking how the patient is feeling. The patient can respond verbally, which will be then processed according to known voice recognition software.

Representative Data/Time Intervals

In addition to entering data for a specific time period (e.g., a day, a week, a month, a year), the patient can enter representative data reflecting how the patient generally feels through the day. This representative day can be compared with aggregates of actual data, which may alert the patient and/or the patient's health care provider to a difference between the patient's perception and reality.

Storage

The method can include the step of storing the entered medical condition metrics, either locally or on a server computer. The server computer can include a memory for storing the metrics e.g., removable memory, such as a compact disk. Storing the metrics can include using a data structure to include entries of the data. The data structure can be stored in a structured data file 132 or in a relational database storage area 134 (see FIG. 1).

Analysis

The method can include the step of analyzing the entered medical condition metrics. The analysis can be done locally or on a server computer. The server computer can include a microprocessor for executing the analysis, for example, the INTEL® x86 microprocessor or a dual-core processor, available from Intel Corporation of Santa Clara, Calif. The analysis can include, for example, normalizing the metrics or converting the metrics to different units.

Graphical Element

Figure 3:
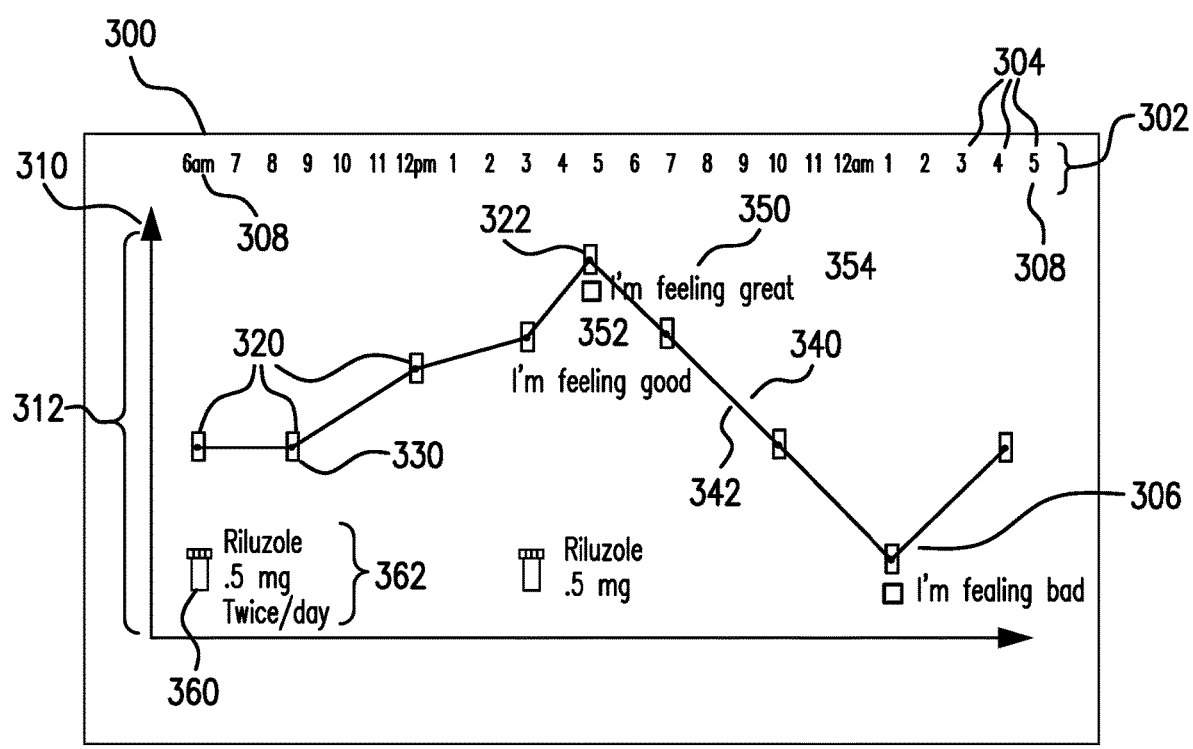
FIG. 3 is a diagram depicting an exemplary graphical element.

The method can include the step of providing a graphical element 300 for displaying the medical condition metrics as shown in FIG. 3. The graphical element can be comprised of other elements for displaying a rich variety of data about a medical condition. The graphical element can include, for example, symbols, figures, icons, colors, backgrounds, widgets and textual information to relate various aspects of the medical condition.

The graphical element can include a time scale 302 showing a series of times 304 at which medical condition metrics were taken. For example, a metric can be taken at 2:00 AM (306). The graphical can include a medical condition metric scale 310. The metric scale includes a range of values 312 for the metric. For example, the range of values for "How are you feeling?" can be from "Great" to "Awful." The graphical element can include one or more points 320, each point display a metric. For example, a point can represent the metric "I'm feeling great!" at 5:00 PM, Jul. 4, 2007 (322). The point is displayed in the graphical element at a location corresponding the metric's position in the range of values along the metric scale and an entered time along the time scale. The entered time can be the time the metric was taken.

Patient Profiles and Medical Outcome Correlations

The method can further include providing a patient profile 210 and a medical correlation outcome 212, as shown in FIG. 2. The patient profile can include personalized data about a patient such as name, sex, and age, and the patient's medical condition. One example of the medical condition is ALS. The patient profile can include medical condition metrics related to the patient's medical condition. For example, the profile can include a set of metrics regarding how an ALS patient is feeling using metrics taken and entered at various times throughout a 24 hour period. A patient may have multiple patient profiles, each representing related medical condition metrics. For example, a patient may be diagnosed with both ALS and depression and may have a profile for both diseases.

The method can provide a medical correlation outcome. A medical outcome correlation is a medical outcome that can be correlated to entered metrics, treatments, daily activities, and other personalized data related to a medical condition. The outcome can be limited to time periods, e.g., 24 hour time periods. For example, a medical outcome correlation for an ALS patient can be: "Show me all the days I felt better-than-average." In the alternative, the medical outcome correlation can be: "Show me all the days I took riluzole in the morning." The medical outcome correlations can be prepackaged or can be customized to entered values. Also, the method may automatically provide the medical outcome correlations as the patient enters medical condition metrics, and views the results.

Figure 4:
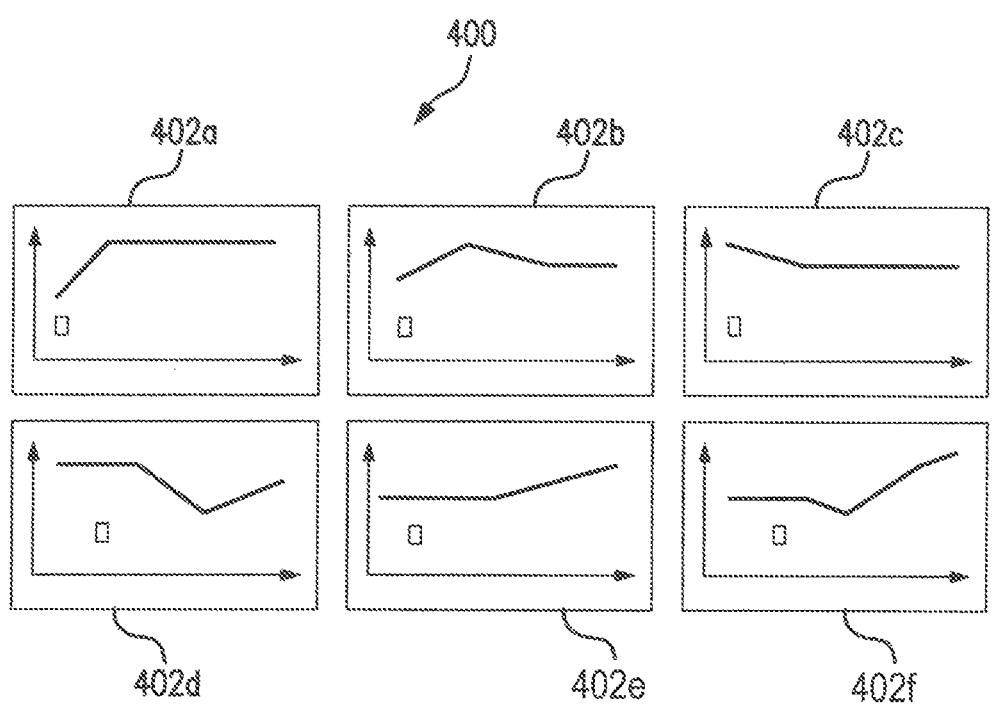
FIG. 4 is a diagram depicting an embodiment of medical outcome correlations.

A medical correlation outcome can be produced by a microprocessor on the server computer executing a server software program for analyzing patient profiles of stored metrics. For example, an ALS patient may want to view all the days he felt better-than-average. The patient can enter the medical outcome correlation and the method can provide a set of displayed metric points matching the outcome in the graphical element. For example, the server software program can search through the patient profiles storing metrics for each day. The server software program can average the metrics and determine that six days match the medical outcome "Show me all the days I felt better-than-average" and provide six displays 400 as shown in FIG. 4. By viewing the days, the patient may notice that on most of the days, he took his treatments early in the day, exercised in the late morning, and ate a light meal at noontime. He may also notice that a nap in the early afternoon helped minimize certain symptoms, such as fatigue or nausea. Thus, he can determine that this general pattern of behavior tends to result in good days. In this way, the method can help a patent self-assess and manage his medical condition and plan his days.

Referring again to FIG. 4, each graphical element 402 can depict a medical condition over time for a particular day or for a plurality of days. For example, if a patient is viewing interface 400 on day n, graphical element 402a can represent day n−1, graphical element 402b can represent day n−2, graphical element 402c can represent day n−3, graphical element 402d can represent day n−4, graphical element 402e can represent day n−5, and graphical element 402f can represent day n−6. In another example, each graphical element can represent an aggregate or average of the medical condition over for a subset of days in which a particular intervention occurred. Graphical element 402a could represent the days on which the patient took a particular medication, while graphical element 402b represented the days on which the patient took a nap in the after, etc.

Point Movement Means

The step of providing a user interface for entering medical condition metrics can further include providing a point movement means for moving metrics points in the graphical element. The point movement means can be a graphical slider 330 attached to a metric point. The slider can also move multiple points. The method can further include an input received from a user, e.g., from a mouse, keyboard, or touch-screen activated by a user. For example, the input can include moving a mouse to select a point, and sliding the mouse in a manner corresponding to upward, downward, leftward, or rightward motion of the point on the graphical element.

Lines Connecting Metric Points

Referring again to FIG. 3, the method can further include providing a line 340 connecting the metric points. The line can be a polyline, i.e., a series of separate line segments 342, each line segment joining adjacent points. The line can be multiple lines, each line joining the metric points for related medical condition metrics or medical outcome correlations. For example, one line can join all the metrics for the medical condition metric, "how am I feeling?", and another line can join all the metrics for the medical condition metric, "trouble swallowing". In this way, an ALS patient can simultaneously view two medical condition metrics entered for a particular day. In another example, a patient diagnosed with Parkinson's Disease can view metrics related to tremors, balance, and muscle stiffness, each metric displayed with a separate polyline. In some instances, the patient may notice that the metrics are correlated or not correlated. For example, balance and muscle stiffness may be correlated because they trend in similar directions throughout the day, or sleepiness and tremors may not be correlated because they trend in opposite directions.

Status Information

The graphical element can include a status element 350 for representing a medical condition metric. The status element can include a color element 352 and a textual description 354. The status element can be displayed in the graphical element at a location adjacent to the related metric point. For example, the status element can be displayed beneath a metric point, the color element can be green to denote a positive status, and can include the description, "I'm feeling great!"

Treatment Information

The graphical element can include a treatment graphical element 360 for representing a treatment of a person. For example, the treatment graphical element can represent riluzole taken by an ALS patient. The treatment graphical element can include a name, a dosage amount, and a treatment frequency 362.

The method can further include the step of providing a list of treatments for a medical condition. For example, the list can include treatments and therapies for Parkinson's Disease, including carbidopa, bromocriptine, rasagiline, surgical interventions, and speech therapy. One or more of the treatments can be selected from the list, dragged, and dropped over a location in the graphical element corresponding to the time of day the treatment was administered to the patient. For example, a mouse can be used to select a treatment element from the list (i.e., press the left mouse button to select), drag the treatment element (i.e., move the mouse while holding the button), and dropped (i.e., release the left mouse button).

The method can further include providing a maximum and a minimum medical condition metric value. For example, the maximum value for a metric degree of mobility can be 100% (i.e., full mobility), and the minimum value can be 0% (i.e., paralysis). Alternatively, the maximum value for how am I feeling metric can be "Great" and the minimum value can be "Awful."

Time Scale

The time scale 302 can further include a start time 308 and an end time 309. For example, the start time can be 6 am, and the end time can be 5:00 AM. The start and end time can be about 24 hours apart, corresponding to about a day, for example 12:00:00 AM on Saturday, Apr. 27, 2007, through 11:59:59 PM on Saturday, Apr. 27, 2007. The start and end time can be about one week or one month apart. Alternatively, the start and end time can include a time span appropriate for the medical condition metric. For example, the start and end time can represent a woman's menstrual cycle.

Interventions

The graphical element can further include an intervention graphical element representing interventions related to the medical condition, education, or training of a person. The interventions can include exercise regimens of a runner training for a track event. For example, the measured time period can include a six month period, ending on the day of the event. The metrics can include time to run a mile and cramping. The interventions can include exercise regimens related to the training, such cardiovascular workouts and weight training. The runner can track his improvement, and determine whether to change his exercise routine.

The interventions can include activities related to food intake, such as snacks or meals. Similarly, a cancer patient measuring nausea and fatigue can also include food intake to determine if particular foods and meal times and affect his nausea and fatigue.

Users

The method can be directed toward a user entering personalized data, including medical condition metrics related to medical condition, and viewing the personalized data using the graphical element as described above. The method steps can be practiced by, for example, a web user. The web user can be a patient diagnosed with a disease, such as Amyotrophic Lateral Sclerosis (ALS), Multiple Sclerosis (MS), Parkinson's Disease, cystic fibrosis, Huntington's Disease, Tourette's Syndrome, heart disease, cancer, Crohn's Disease or other life-changing illnesses. The web user can also be a nurse or doctor of the patient or clinician conducting research.

Figure 5:
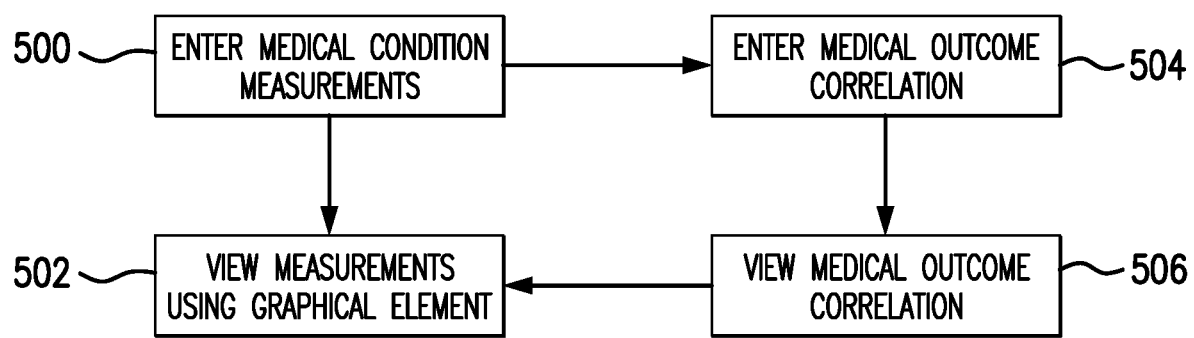
FIG. 5 is a diagram depicting a method of practicing the invention by a user.

As shown in FIG. 5, the method can include the steps of entering medical condition metrics 500, and viewing the medical condition metrics using the a graphical element 502 as described above. The method can further include entering a medical outcome correlation 504, for example, "Show me all the day during which I felt better-than-average," and viewing the medical outcome correlation using the graphical element 506.

Intervention Timing

The invention can aid patients in adherence to prescription instructions. The invention can include manufacturer's prescribing information for one or more medications or may be able to access such information through sources such as the *Physician's Desk Reference*, available from Thomson Corporation of Toronto, Ontario. When a patient enters information about an intervention such as taking a medication or eating, the invention can review these intervention to determine if the timing is in accordance with the manufacturer's prescribing information. For example, if a patient consumes a medication with a meal, the user interface may advise the patient that the particular medication should be taken an hour before eating.

Data Structure

Figure 6:
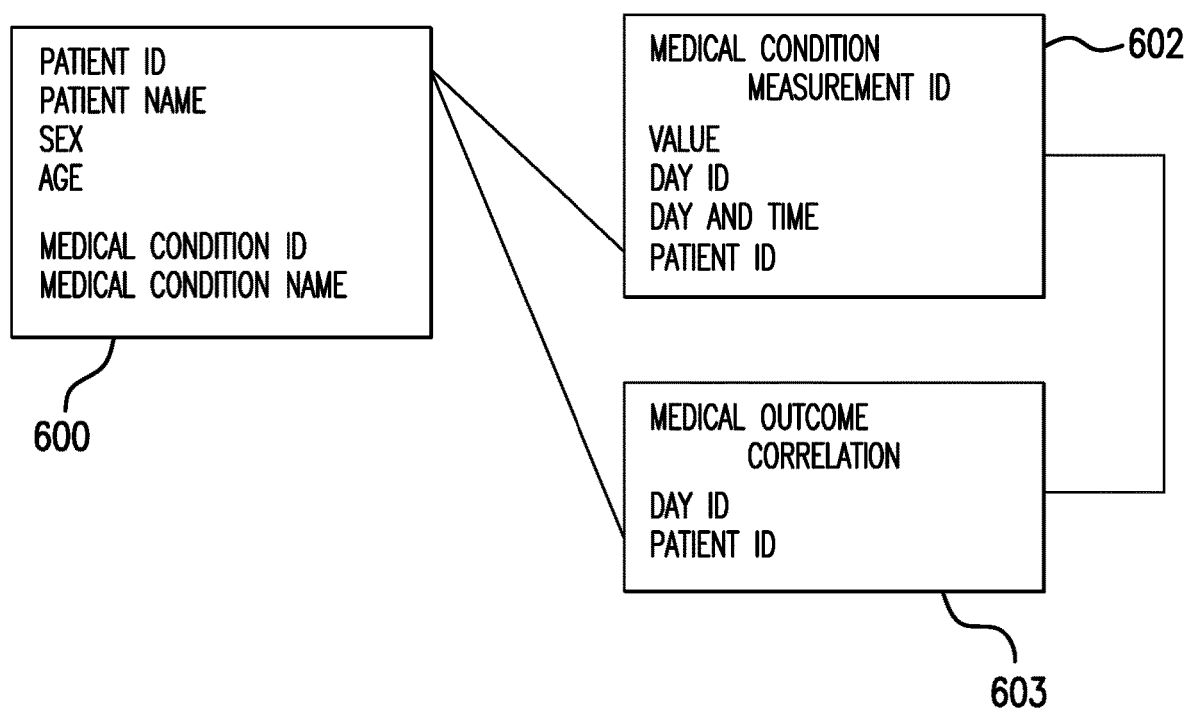
FIG. 6 is a diagram depicting a data structure directed toward the invention.

The invention can be directed toward a computer-readable medium device for encoding a data structure. As shown in FIG. 6, the data structure can include entries for personalized data of a person and a medical condition of the person 600. These entries can include the person's name, age, sex, age, and a medical condition of the person, such as ALS. The person can have a unique identifier stored in the data structure. The medical condition can also have a unique identifier stored in the data structure. The data structure can include entries for medical condition metrics 602 related to a person's medical condition, for example, a medical condition metric can be irritability related to a person with bipolar disorder. The data structure can include metric values, the day the metric was taken, and the time of day the metric was taken. The data structure can include entries for a medical outcome correlation 603.

The data structure entries can be transferred from a memory located on a server computer to a client computer to execute functions of a client software program. Alternatively, the client software computer can transfer entered values, such as medical condition metrics, to the server computer. The server computer can store the entered values in the data structure for use later. The computer-readable medium device can be physically shipped with a software program.

Additional User Interface Embodiments

Figure 7:
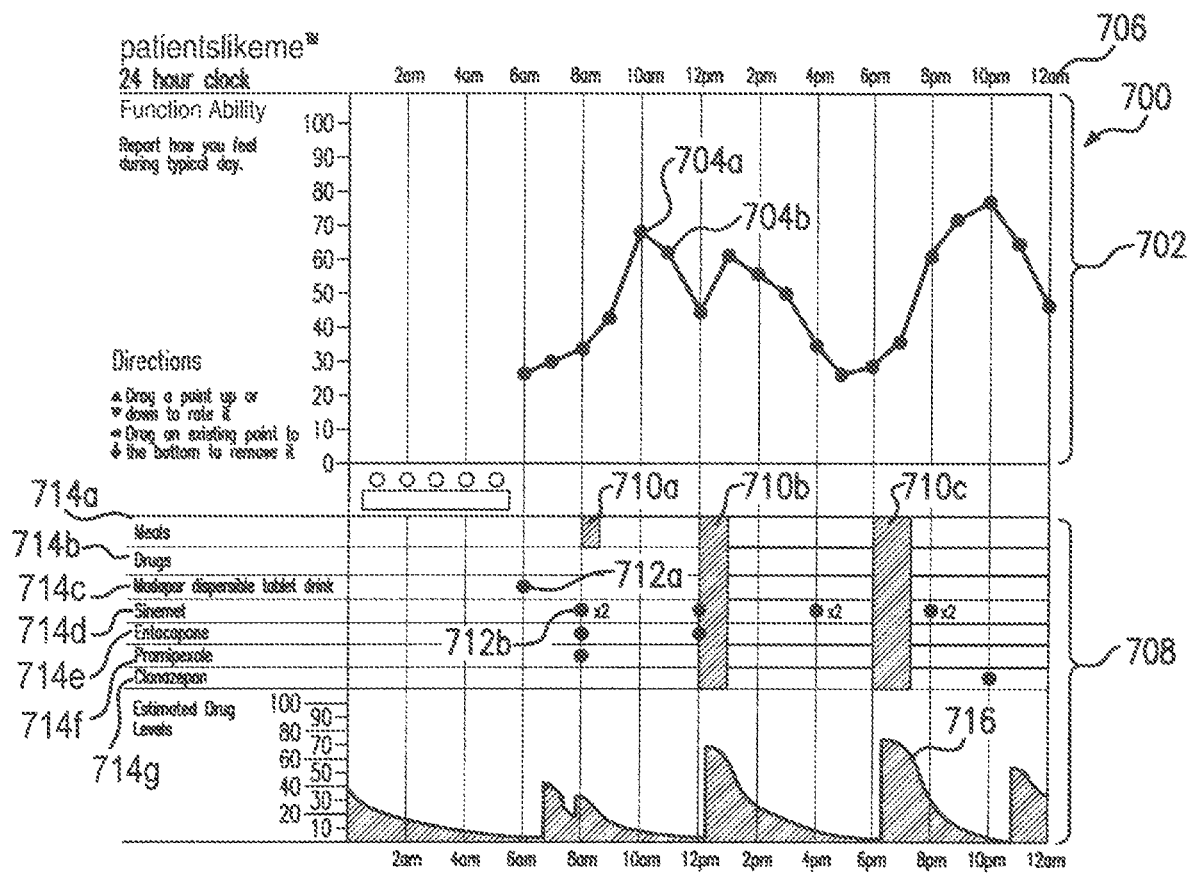
FIG. 7 is a diagram depicting another exemplary graphical element.

Referring now to FIG. 7, another exemplary user interface 700 is provided. Although user interface 700 is customized for a patient suffering from Parkinson's disease, the principles explained and depicted herein are equally applicable to any disease.

User interface 700 includes a medical condition metric portion 702, which allows the patient to input a medical condition metric (in this example, the patient's functional ability). The user can place multiple data points 704 in the medical condition metric chart, which includes a time scale. Data points 704 can be adjusted with respect to time and/or magnitude. For example, if the patient is indicating how she feels now or at a designated time, the patient can be limited to moving data point 704 up or down. Alternatively, the patient can input data for a time by dragging the data point to the left or right. The patient can be restricted in some embodiments from setting a data point in the future.

User interface 700 also includes an intervention portion 708. Intervention portion 708 allows the patient to record one or more interventions such as administration of a medication, administration of a remedy, administration of a nutritional supplement, administration of a vitamin, exercise, physical therapy, massage, stretching, consumption of food, rest, and sleep. For example, the patient can designate when meals are eaten by adjusting bars 710*a*, 710*b*, 710*c* to indicate the beginning and ending of the meal. Likewise, the patient can indicate when one or more drugs 714*a*-714*g* are administered by placing markers 712 (which may depict pills) on a time scale.

Various types of remedies can be scheduled for specific times. For example, the patient can be prescribed to take madopar at 6:00 AM In this situation, user interface 700 can display a medication schedule. The patient can modify this schedule to reflect the actually administration by dragging marker 712*a*. Likewise, the patient can indicate that the drug was consumed by clicking on the marker 712*a*. Clicking on the marker can change the appearance of the marker 712*a* (e.g., its color) and thus can be used by patients, particularly patients with memory problems, to more faithfully follow a medication program.

User interface 700 can also include pharmacokinetic data, such a pharmacokinetic curve 716 that depicts the concentration of a medication within the patient over time. Multiple pharmacokinetic curves 716 can be depicted in various colors or patterns to reflect varying pharmacokinetic properties of various medications.

Slider Bar

Figure 8A:
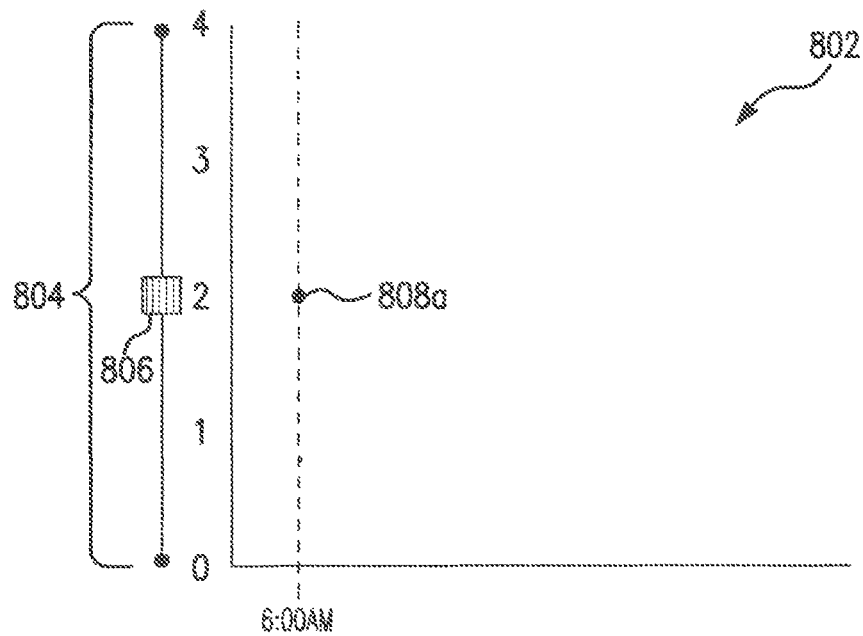
FIGS. 8A-8D are diagrams depicting the functionality of a slider bar element.

Referring to FIGS. 8A-8D, an embodiment of a user interface is provided. As in FIG. 7, a medical condition metric portion 802 is provided. In FIG. 8A, the first medical condition metric is recorded for a day. The patient either indicates that she wishes to record metric from 6:00 AM or accesses the user interface at 6:00 AM at which point the user interface can default to 6:00 AM. The patient manipulates slider bar 804 to input a medical condition metric. For example, if the patient wishes to indicate that '2' is the medical metric (e.g., a measurement of pain on a scale from 0-4), the user drags handle 806 the slider bar 804 to the '2' position as depicted in FIG. 8A.

Data point 806*a* can move up and down along vertical line 808*a* as the handle 806 is moved or data point 806*a* may not appear until the medical condition metric is finalized. A metric can be "finalized" in a number of ways, including by clicking the handle 806 to lock the handle 806. Additionally or alternatively, the metric can be finalized by a period of inactivity, for example, about fifteen seconds, about thirty seconds, and about one minute.

Figure 8B:
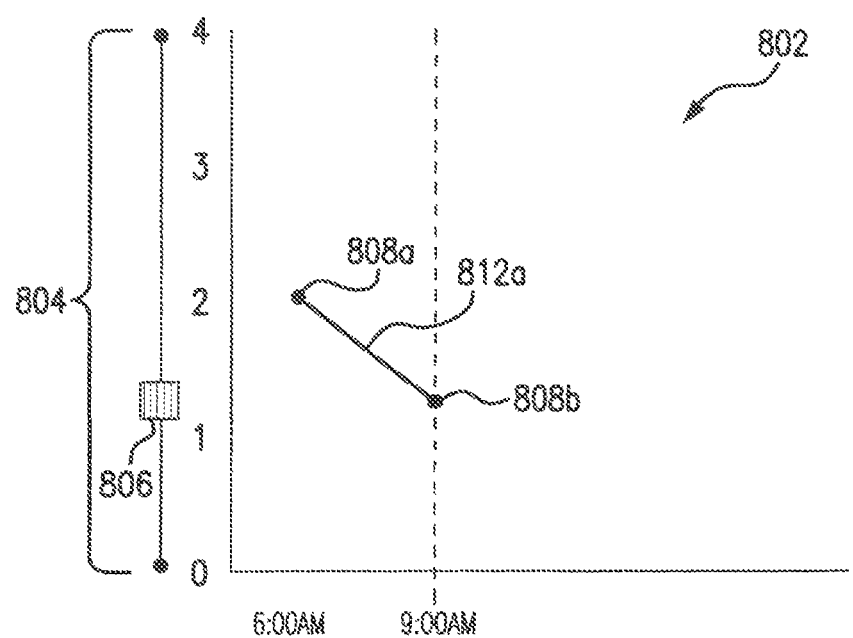
Figure 8C:
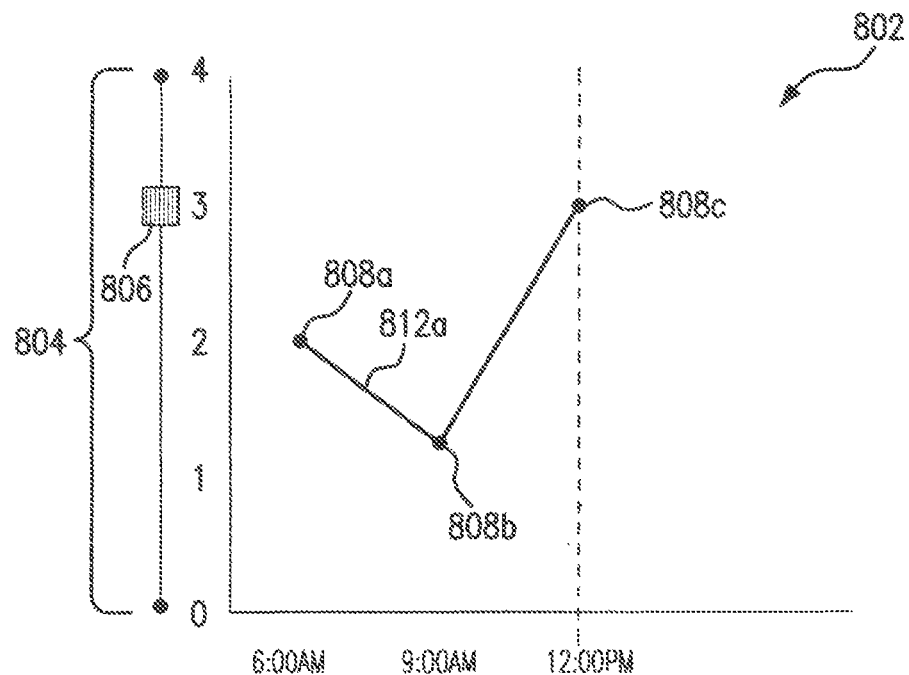

Referring now to FIG. 8B, the patient enters a second medical condition metric. The patient again moves the handle 806 of the slider bar 804. If the system is configured so that the data point 808*b* moves with the handle 806, line segment 812*a* also moves. Thus, the patient can readily see whether they are indicating that a medical condition metric is improving or deteriorating and verify that such a change truly reflects their experience.

As discussed in the context of FIG. 8A, the patient can indicate that she wishes to record metrics from 9:00 AM or can access the user interface at 9:00 AM at which point the user interface can default to 9:00 AM. The patient can leave the user interface open for a period of time and the patient can continue to access the user interface and manipulate the slider bar. Each time the user manipulates the slider bar 804, a new data point can be set for that time that the slider bar is manipulated.

Referring to FIG. 8C, the patient again manipulates the slider bar 804 to enter a third data point 808*c* and form a new line segment 812*b*.

Figure 8D:
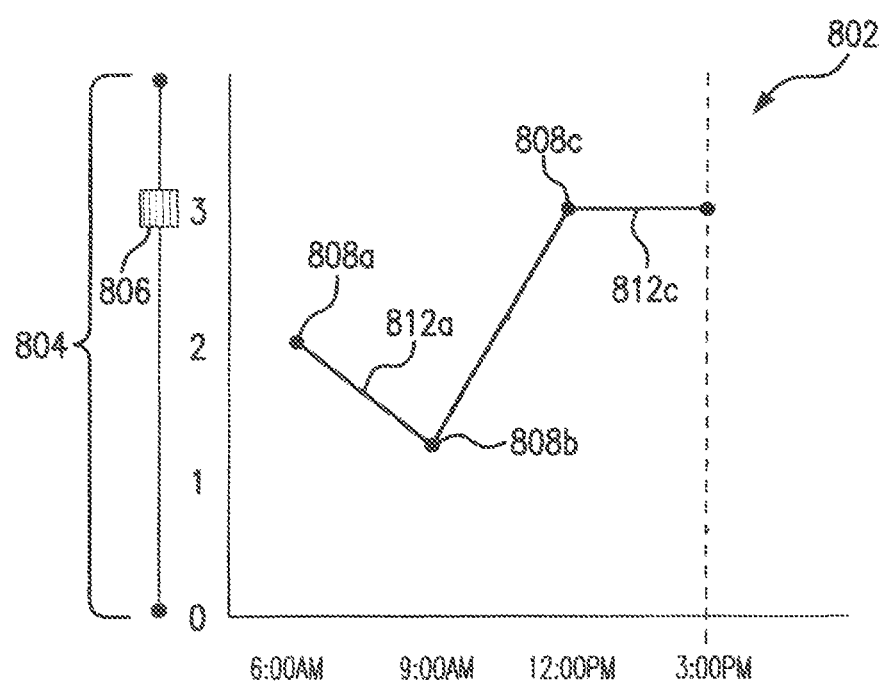

Referring to FIG. 8D, the patient indicates that the medical condition remains a '3' at 3:00 PM. The slider bar handle 806 can remains at the '3' position from the 12:00 PM data entry. The patient can indicate that the metric remains a '3' by clicking on the handle 306 to lock the slider bar 304. During this, line segment 812*c* can grow horizontally from data point 808*c* as time progresses from 12:00 PM. Otherwise, the slider bar handle 806 can disappear after data point 808*c* is set. Handle 806 reappears when the patient clicks or moves the mouse over the slider bar 804.

Application to Depression

Some modern theories of depression posit that depression results from cognitive distortions. While all individuals become sad or upset at some points in time, most individuals have the perspective to recognize that such feeling are short-lived. However, individuals with a major depressive disorder are thought by some to lack the ability to recognize recall a time before they entered a depressive episode, and therefore cannot anticipate better times in the future.

The invention described herein are capable of helping persons dealing with depression. Depressed persons can enter their mood or other medical condition metrics into the systems described herein and retrieve graphical representations of these metrics over time. Such a system provides external memory and perspective for the patient.

Furthermore, the inventions described herein can be used by generally healthy individuals in advance of disease. For example, military personnel can record medical condition metrics before deployment to an armed conflict. Such prior medical condition metrics can serve both as a reference point for the military personnel when coping with conditions such a post traumatic stress disorder (PTSD) and to military health personnel seeking to screen for PTSD.

The functions of several elements can, in alternative embodiments, be carried out by fewer elements, or a single element. Similarly, any functional element can perform fewer, or different, operations than those described with respect to the illustrated embodiment. Also, functional elements (e.g., modules, databases, computers, clients, servers, and the like) shown as distinct for purposes of illustration can be incorporated within other functional elements, separated in different hardware or distributed in a particular implementation.

While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein.

INCORPORATION BY REFERENCE

All patents, published patent applications, and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Specifically, although this application periodically discusses the application of the invention to "diseases", the invention is equally applicable to other medical events such as aging, fertility, and the like. Such equivalents are intended to be encompassed by the following claims.

What is claimed is:

1. A method for providing a graphical user interface for graphically illustrating personalized management of a medical condition, the method comprising:
    providing a graphical user interface having a:
        medical condition portion for allowing the patient to input multiple data points relating to at least first and second medical conditions; and
        medical intervention portion for allowing the patient to input multiple data points relating to a medical intervention associated with the medical condition;
    adjusting on the graphical user interface the multiple data points relating to the at least first and second medical conditions with respect to time and magnitude wherein each data point is adjustable on a first axis representative of time and on a second axis representative of magnitude wherein a line connects each data point to one another for each respective at least first and second medical conditions such that the line moves upon user adjustment of the multiple data points;
    adjusting on the graphical user interface the multiple data points relating to the medical intervention with respect to time;
    displaying on the single display the at least first and second medical condition metrics and intervention over the time interval which includes pharmacokinetic data depicting concentration of a medication relative to a patient over time including at least one pharmacokinetic curve representative of pharmacokinetic properties relative to one or more medications;
    receiving an additional medical condition metric measured by a medical device wherein the at least one medical condition metric is observed by the patient and wherein the intervention includes at least one selected from the group consisting of: administration of a medication, administration of a remedy, administration of a nutritional supplement, administration of a vitamin, exercise, physical therapy, massage, stretching, consumption of food, rest, and sleep;
    calculating a correlation between the at least one intervention and the at least one medical condition metric; and
    displaying on a single display the additional medical condition metric in conjunction with the: 1) at least first and second medical conditions; 2) the medical intervention; and 3) the pharmacokinetic curve.

2. The method of claim 1, wherein the graphical user interface includes a line chart representing the multiple data points.

3. The method of claim 2, wherein time is depicted on the x-axis of the chart.

4. The method of claim 1, wherein the time interval is one selected from the group consisting of: 24 hours, 1 week, and 1 month.

5. The method of claim 2, wherein the chart displays data from multiple time periods.

6. The method of claim 2, wherein providing a graphical element includes displaying a plurality of charts, each of the plurality of charts displaying information for a different time interval.

7. The method of claim 1, wherein the graphical element includes a slider bar for inputting a medical condition metric.

8. The method of claim 1, wherein the medical condition is one selected from the group consisting of: movement disorders including parkinsonism, pain disorders including back pain, migraines, fibromyalgia, fatigue disorders, mood disorders including depression and anxiety, eating disorders, and seizure disorders including epilepsy.

9. The method of claim 1, wherein the at least one medical condition metric is received from a mobile device.

10. The method of claim 1, wherein the time interval is an actual time interval.

* * * * *